United States Patent [19]

Inglefield, Jr.

[11] 4,351,334

[45] Sep. 28, 1982

[54] SAFETY DEVICE FOR SECURING THUMB OR FINGER TO A SYRINGE

[76] Inventor: Joseph T. Inglefield, Jr., 210 E. Broad St., Falls Church, Va. 22046; Joseph T. Inglefield III, 4923 Arbor Ridge, San Antonia, Tex. 78228; Effie J. Heulitt, 343A Ogden Ave., Jersey City, N.J. 07307; David L. Inglefield, 6329 Linway Terr., McLean, Va. 22101

[21] Appl. No.: 217,563

[22] Filed: Dec. 17, 1980

[51] Int. Cl.³ .............................................. A61M 5/00
[52] U.S. Cl. .............................................. 128/218 PA
[58] Field of Search ......... 128/218 R, 218 P, 218 PA, 128/215, 216, 234, 213

[56] References Cited

U.S. PATENT DOCUMENTS 2,823,675  2/1958  Sciurba ...................... 128/218 PA
2,842,128  7/1958  Hein, Jr. ..................... 128/218 PA
4,217,896  8/1980  Behnke ........................ 128/218 PA

FOREIGN PATENT DOCUMENTS 1181162  6/1959  France ........................ 128/218 PA
 795202  5/1958  United Kingdom ......... 128/218 PA Primary Examiner—John D. Yasko
Attorney, Agent, or Firm—Lane, Aitken, Kice & Kananen

[57] ABSTRACT

A digital safety device comprises a tubular member which fits snugly on the thumb or finger and includes a slot which quickly and securely receives the plunger of a conventional syringe. The slot is larger than the cross section of the plunger, but smaller than the head of the plunger, so that the plunger is retained in the tubular member and moves with the thumb in both the retracting and injecting directions. An inwardly tapering conical portion is defined at one end of the tubular member, so that the end fits snugly on the tapering portion of the thumb or finger. The slot allows quick and easy disengagement of the used plunger and syringe, while the safety device remains on the thumb or finger, ready to conveniently accept a new syringe with its plunger. An outwardly directed annular flange is provided on the tubular member to define a gripping formation, so that the digital device may be easily grasped for placement on or removal from the thumb or finger.

15 Claims, 13 Drawing Figures

SAFETY DEVICE FOR SECURING THUMB OR FINGER TO A SYRINGE

BACKGROUND OF THE INVENTION

This invention relates to a thumb or finger (digital) device for attachment to a syringe, and more particularly, to a digital device comprising a tubular member attachable to the plunger of a syringe for a single-handed control of the movement of the plunger both into and out of the barrel of the syringe.

In making subcutaneous injections of certain biologicals, a grave hazard exists from the possibility that the biological can be unintentionally injected directly into a blood vessel. When a biological is injected directly into the blood stream, a generalized reaction can occur due to the extent and rapidity of the distribution of the biological material and the rapidity of the patient's reaction thereto. In order to eliminate, or at least minimize, this hazard, it is a recommended procedure that after inserting a syringe needle to make an injection, the plunger of the syringe is withdrawn a small amount to create a negative pressure within the injection chamber. If the needle point opening of the syringe has been accidentally placed within the lumen of a blood vessel, the negative pressure within the injection chamber would draw blood immediately into the syringe and, thus, provide an immediate signal to the person making the injection to terminate the procedure before the biological material contained within the injection chamber is injected. If the negative pressure yields no blood return, then it may be presumed that the needle point opening is positioned outside of any blood vessel and the biological material may be safely injected into the subcutaneous or intramuscular space where the open end of the needle point has been placed. Because it is an awkward procedure to first withdraw the plunger before injecting the biological material, the technician, nurse or physician frequently will omit this initial safety maneuver and will directly inject the biological material and run the risk of intravascular injection at the patient's hazard.

The present invention eliminates this awkwardness and provides a simple, quick and effective means not only for accomplishing withdrawal of the syringe barrel, but also the stabilization of the needle point opening in the tissues where it has been inserted. This is achieved in accordance with the invention by means of an open-ended unitary tubular member which provides a secure attachment of the head of the plunger to the thumb or finger of the person performing the injection.

Prior to the present invention, it was known to provide a thumb ring on the exposed end of a plunger of a syringe to permit the control of the movement of the plunger in both the injecting and retracting directions and such a structure would facilitate withdrawal after the needle has been inserted without the person making the injection needing to change his grip on the syringe. However, the inclusion of a thumb ring on each syringe adds to the manufacturing cost of the syringe, a factor which is particularly important with respect to disposable syringes, which are now used with increasing frequency, especially where large numbers of injections must be made, such as in hospitals. Such disposable syringes can be manufactured in sterile conditions and packaged in sterile containers prior to delivery to the point of use, and can even be prefilled with a medicinal fluid at the factory. This provision of a ring integral with the plunger on each syringe would significantly add to the cost of producing the syringes, as well as adding to the sizes of packages needed to ship and store the syringes.

Previous attempts have been made to provide detachable devices for controlling the movement of syringe plungers. Some of these prior art devices require special plunger configurations with which to mate. For example, U.S. Pat. No. 3,815,785 to Gilmont discloses a ring attached to a plunger by means of an internally threaded axial bore in the plunger. U.S. Pat. No. 1,279,069 to Yoshida requires a two-piece plunger including an inner member slideable within an outer member, in which the head of the plunger is formed on the inner member and an additional flange is formed adjacent thereto. In addition, a second additional flange is formed at the open end of the outer member, both of the additional flanges being required to maintain a detachable thumb-engageable member on the plunger.

Other prior detachable devices require the removal of the device from the thumb and a somewhat time-consuming procedure for attaching and detaching the device to the plunger of the syringe. For example, U.S. Pat. No. 2,842,128 to Hein, Jr. discloses a ring member including two arms which are threaded at one end and provided with grooves at the other end for receiving the head of the plunger. The threaded ends are received in opposite ends of a threaded sleeve and are forced toward one another upon rotation of the sleeve, whereby the grooved ends tighten around the head of the plunger. U.S. Pat. No. 2,882,901 to De Venezia discloses a ring member attached to the head of a plunger by means of a threaded retaining ring. The ring member has a cup-shaped extension having exterior threads which cooperate with interior threads formed on the retaining ring. The retaining ring has an inner diameter which is larger than the diameter of the plunger but smaller than the diameter of the head, so that the positioning of the retaining ring on the plunger requires the removal of the plunger from the barrel of the syringe. The detachment of the ring members disclosed in such prior art devices and their attachment to filled syringes constitutes an inconvenient and time-consuming procedure, especially where large numbers of injections must be administered within a very brief interval of time as in an allergist's office.

SUMMARY OF THE INVENTION

It is, therefore, an object of the present invention to provide a detachable digital device for the plunger of a syringe which provides one-handed control of the movement of the syringe plunger in both the injection and retraction directions.

It is another object of the present invention to provide a detachable digital device which is easily attachable to and detachable from the plunger of a syringe while the device is in position on the thumb or finger of a user.

It is a further object of the present invention to provide a detachable digital device which is attachable to and detachable from syringes having conventional plungers.

It is a still further object of the present invention to provide a detachable digital device for attachment to the plunger of a syringe, having a one piece structure which is inexpensive to produce.

It is a further object of the present invention to provide a detachable digital device, which provides a secure attachment of the head of the syringe plunger to the thumb or finger of the person performing the injection and which accomplishes stabilization of the needle point opening in the tissues after the needle has been inserted.

Toward the fulfillment of these and other objects, the detachable digital device of the present invention comprises an open-ended unitary tubular member formed from a flexible plastic material. The tubular member includes a cylindrical portion, a frustoconical portion adjacent to the cylindrical portion and defining a small open end of the tubular member and a flange formed on the cylindrical portion at the other large open end of the tubular member. A lateral slot is defined in the tubular member and extends from a closed terminus intermiediate the ends to an open terminus at the small end. Various embodiments of the device having different slot configurations are contemplated, all of which permit easy attachment to and detachment from the plunger of the syringe while the device is in position on the thumb or finger of a user. The frustoconical portion tapers inwardly toward the axis of the tubular member and, in some embodiments of the device, allows the device to accommodate the taper of the end of the thumb or finger.

Among the various lateral slot configurations contemplated by the invention is a slot having a constant width from its closed terminus to its open terminus.

In another embodiment, the slot tapers in width from its closed terminus to its open terminus, so that the portions of the tubular member bordering the narrower part of the slot are deflected by the plunger of the syringe as the device is slipped onto a syringe, the boardering portions springing back into place when the plunger passes to the wide end of the slot, thereby retaining the plunger in the slot.

In still another embodiment of the present invention, the slot includes an opening, formed intermediate the ends of the tubular member, which is complementary to the cross section of the plunger, and a slit extending from the complementary opening to the small end of the tubular member. The plunger of a syringe is forced into the slit, thereby separating the flexible material bordering the slit, and into the complementary opening, in which the plunger is firmly held when the material bordering the slit springs back into place.

In yet another embodiment, the slot is T-shaped, including a stem portion defining the open terminus at the small end of the tubular member and communicating with a narrow opening transverse to the stem portion and defining the closed terminus of the slot intermediate the large and small ends. A web is formed across a portion of the small end of the tubular member adjacent to the open terminus of the slot, and has an aperture which includes an open terminus at the juncture of the web and the frustoconical portion, and a closed terminus in a central area of the web. The aperture has a width equal to the width of the stem portion and is in alignment with and in communication with the stem portion, whereby the plunger of a syringe may be held in a position parallel to the axis of the tubular member and moved toward the axis so that the head of the plunger passes through the narrow transverse opening and the plunger passes through the stem portion of the slot until the leading side of the plunger engages the closed end of the aperture in the web. At this point, the plunger may be swung away from the axis of the tubular member and toward the narrow transverse opening until the plunger is approximately perpendicular to the axis of the tubular member, which is its operational position.

In a further embodiment of the present invention, the slot has a shape which is congruent to half of the cross section of the plunger of a syringe. A web extends across a portion of the small end of the tubular member and includes an edge and an aperture in alignment with and in communication with the slot, which aperture is congruent to the other half of the cross section of the plunger. A slit is defined in the web and extends between the edge of the web and the web aperture, so that the plunger may be forced between the portions of the web on either side of the slit and into position in a complementary socket defined by the slot and the web aperture together.

In each of the aforementioned embodiments, the device according to the present invention provides engagement between the thumb or finger of the user and the head of the plunger, so that the thumb or finger can impart a force on the plunger in the injection direction. When the thumb or finger is moved in the retraction direction, the device moves with it and the head of the plunger is retained in the slot, so that the plunger also moves in the retraction direction.

In another embodiment of the invention designed for use with syringes with large heads, such as 3 cc. or 5 cc. syringes, no aperture is formed through the wall of the tubular device, but the device is molded to provide a slot outside the inner diameter of the device, which slot is shaped to receive the enlarged head of the plunger. This construction is used for an enlarged head syringe to avoid the weakening of the structure that would result from an enlarged slot or aperture formed through the wall of the tubular device to accommodate the enlarged head of the plunger.

In all of the embodiments, the flange is provided on the tubular member at the large end to define a surface which may be easily gripped to place on or to remove the tubular member from the thumb or finger.

A set of digital devices of various sizes to fit various sizes of thumbs or fingers can be provided with each order of syringes of a certain minimum number, such as a gross. The entire set of digital devices can be inexpensively molded in one piece, with the individual digital devices attached to a single common member by frangible connections. At the time of use, the digital device of the proper size can be pulled from the common member and placed on the thumb or finger for attachment to a syringe.

DETAILED DESCRIPTION OF THE PREFERRED EMBODIMENT

Figure 1:
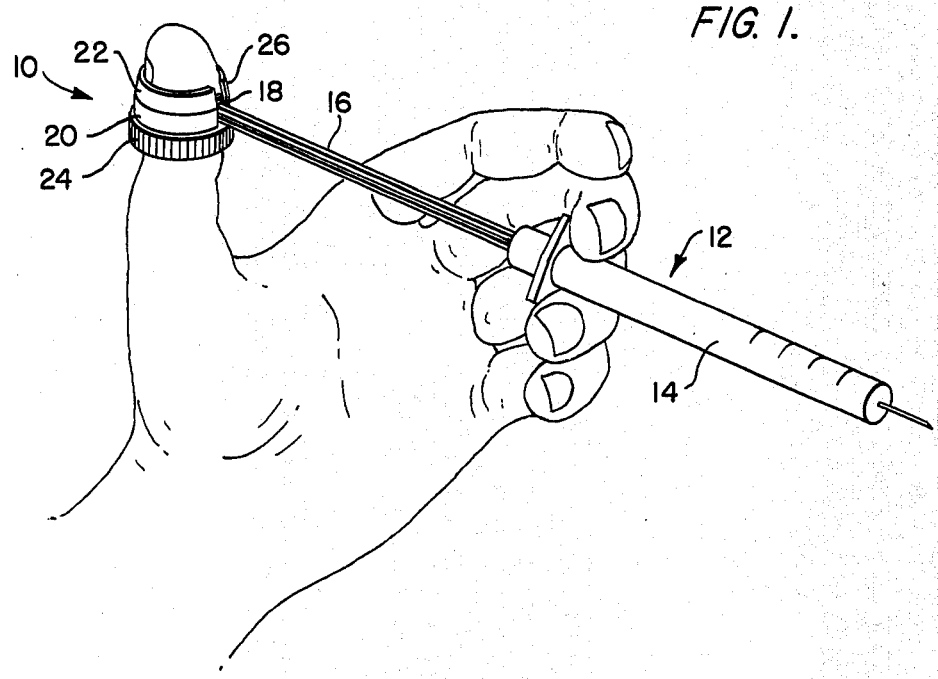
FIG. 1 is a perspective view of an embodiment of the digital device according to the present invention connected to the plunger of a syringe for controlling the movement thereof.

As shown in FIG. 1, the digital device according to the present invention comprises a tubular member, generally designated by the reference numeral 10, which is attachable to a conventional syringe 12 of either a disposable or reusable type. The syringe 12 typically includes a barrel 14 having a pair of finger lugs, finger rings, or some other structure which is adapted to be engaged by the fingers of a hand of a user. The syringe 12 also typically includes a plunger 16 having one end positioned within the barrel 14 for reciprocation therein and another end projecting from the barrel and terminating in a head 18 for engagement by the thumb of a user.

The tubular member 10 is made of a flexible plastic material and includes a cylindrical portion 20, an inwardly tapering frustoconical portion 22 formed at one end of the cylindrical portion 20 and defining a small open end of the tubular member 10, and a radially outwardly extending flange defining a gripping formation 24 integrally formed on the cylindrical portion 20 at the other, large open end of the tubular member 10. The gripping formation 24 may include a series of ribs or may be knurled or otherwise roughened to aid the gripping of the tubular member 10. The tubular member 10 further comprises a lateral slot 26 for receiving and retaining the plunger 16 of the syringe 12.

Figure 2:
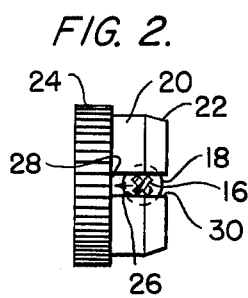
FIG. 2 is a side elevational view of the embodiment of the digital device of FIG. 1.

As is illustrated in FIG. 2, in a preferred embodiment of the digital device, the slot 26 extends from a closed terminus 28 adjacent to the gripping formation 24 to an open terminus 30 passing through the frustoconical portion 22 at the small end of the tubular member 10. The slot 26 has a width which is constant throughout its length and is greater in dimension than the width of the plunger 16 but less than the width of the head 18. Therefore, the plunger 16 of a syringe 12 can be received in the open terminus 30 of the slot 26 and can be moved toward the gripping member 24 until it engages the closed terminus 28 of the slot 26, wherein the head 18 is positioned within the tubular member 10 and is prevented from passing through the tubular member 10 in a radial direction.

Figure 3:
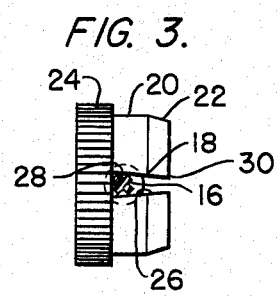
FIG. 3 is a side elevational view of another embodiment of the digital device according to the present invention.

In an alternate preferred embodiment, as is shown in FIG. 3, the digital device is the same as the embodiment shown in FIG. 2 except that the slot 26 is tapered from a width greater than the width of the plunger 16 at the closed terminus 28 of the slot 26 to a width less than the cross section of the plunger 16 at the open terminus 30 of the slot 26. As a result, the insertion of the plunger 16 into the slot 26 requires the separation of the material of the tubular member 10 which borders the slot 26. This separation is permitted by the flexibility of the plastic material of which the tubular member 10 is formed, which allows the material to be deflected away from the slot 26 as the plunger 16 passes therethrough and also causes the material to spring back to its original position as the plunger 16 is moved to the closed terminus 28 of the slot 26. The tapering of the slot 26 and the resiliency of the material of the tubular member 10 aid in retaining the plunger 16 at the closed terminus 28 of the slot 26 and prevent the sliding of the plunger 28 toward the open terminus 30.

Figure 4:
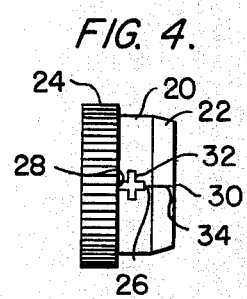
FIG. 4 is a side elevational view of still another embodiment of the digital device according to the present invention.

In another preferred embodiment of the digital device according to the present invention, as is illustrated in FIG. 4, the slot 26 comprises an opening 32 in the cylindrical portion 20 adjacent to its closed terminus 28 having a configuration corresponding to the cross section of the plunger 16 of the syringe 12 and a slit 34 extending from the opening 32 through the frustoconical portion 22 to the open terminus 30 of the slot 26. As the plunger 16 of the syringe 12 is moved through the slit 34, the material of the tubular member 10 bordering the slit 34 is separated by the wedging action of the plunger 16, whereupon the plunger 16 may pass into the opening 32, which is configured in a shape to correspond to the cross section of the plunger 16. When the plunger 16 has moved into the opening 32, the material bordering the slit 34 moves back into its original or relaxed position due to its own inherent resiliency. Since the syringe 12 illustrated in the drawings includes a plunger 16 having a cruciform cross section, the opening 32 has a corresponding cruciform shape, although it is understood that the opening 32 can be made in shape of a circle, rectangle or other form to correspond to plungers having other cross sections. As in the previous embodiments, the plunger 16 is prevented from passing through the tubular member 10 in a radial direction due to the fact that the head 18 of the plunger 16 is wider than the width of the slot 26. In addition, the plunger 16 is retained firmly within the opening 32 and is prevented from sliding laterally out of the opening 32 by the resiliency of the material bordering the slit 34.

Figure 5:
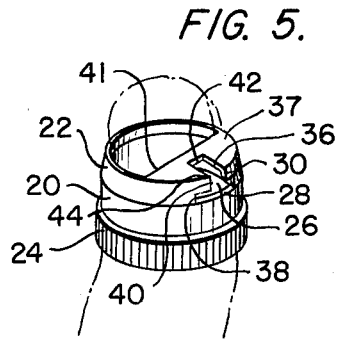
FIG. 5 is a perspective view of yet another embodiment of the digital device shown in position on a thumb.
Figure 6:
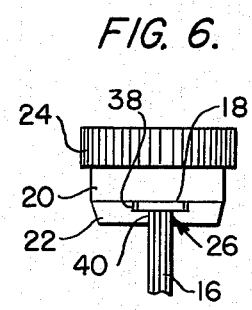
FIG. 6 is an elevational view of the digital device of FIG. 5 showing a portion of a plunger of a syringe in position for insertion into a slot in the digital device.
Figure 7:
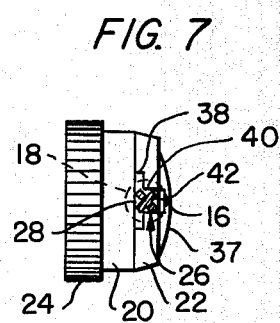
FIG. 7 is an elevational view of the digital device of FIG. 5, showing the plunger of a syringe in position for operation.

Still another preferred embodiment of the digital device according to the present invention, which is represented in FIGS. 5-7, includes a slot 26 having a T-shape and a coacting aperture 36 defined in a web 37 formed across a portion of the small end of the tubular member 10. As is shown in FIG. 5, the digital device is in position on the thumb of a user and includes the T-shaped slot 26 formed in the frusto-conical portion 22. The T-shaped slot 26 includes a head section comprising a narrow transverse opening 38 formed in the frusto-conical section 22 adjacent to the cylindrical section 20 at the closed terminus 28 of the slot 26 and a stem section 40 perpendicular to the transverse opening 38, extending from the transverse opening 38 to the open terminus 30 at the small end of the tubular member 10. The web 37 is formed integrally with the frustoconical portion 22 across a portion of the small end of the tubular member 10 and defines the aperture 36 in alignment with the stem section 40 of the T-shaped slot 26 and an edge 41 extending along a chord of the small end. The aperture 36 has the same width as the stem section 40 and extends from a closed terminus 42 in a central area of the web 37 to an open terminus 44 communicating with the open terminus 30 of the T-shaped slot 26, thereby forming a continous opening from the closed terminus 28 of the T-shaped slot 26 of the closed terminus 42 of the aperture 36.

FIG. 6 shows a portion of the plunger 16 and the head 18 of the plunger 16 in position for insertion into the T-shaped slot 26 of the digital device embodiment shown in FIG. 5. The head 18 of the plunger 16 fits within the transverse opening 38, and the plunger 16 is received within the stem section 40 when the axis of the plunger 16 is parallel to the axis of the tubular member 10. At this point, the plunger 16 is positioned at the open terminus 44 of the aperture 36 in the web 37, from which it is moved to the closed terminus 42 of the aperture 36. When the plunger 16 is in abutment with the closed terminus 42, it is pivoted relative to the tubular member 10 within the continuous opening formed by the T-shaped slot 26 and the aperture 36 so that the head 18 of the plunger 16 remains within the tubular member 10 and the plunger 16 is in engagement with the closed terminus of the T-shaped slot 26, as is illustrated in FIG. 7. This is the operative position of the plunger 16 in the tubular member 10, in which the head 18 of the plunger 16 extends beyond the frustoconical portion 22 and is accommodated by the outward deflection of the web 37. In this embodiment, as in the other embodiments, in the operative position of the plunger 16 in the tubular member 10, the head 18 is too large to pass radially outwardly through the slot 26.

Figure 8:
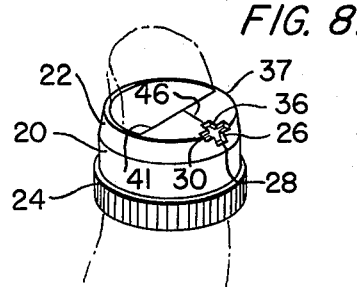
FIG. 8 is a perspective view of a further embodiment of a digital device according to the present invention shown in position on a thumb.
Figure 9:
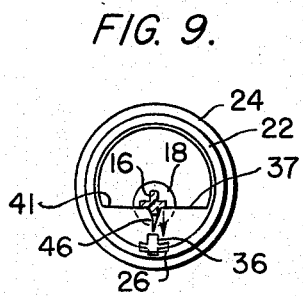
FIG. 9 is a plan view of the digital device of FIG. 8 showing the plunger of a syringe in position for insertion into a slot in the digital device.
Figure 10:
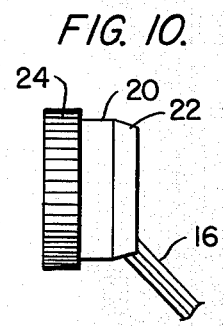
FIG. 10 is an elevational view of the digital device of FIG. 8 showing a portion of the plunger in position in a slot formed in the digital device.

In still another preferred embodiment of the digital device according to the present invention, as is illustrated in FIGS. 8-10, the slot 26 is formed in the frustoconical portion 22 of the tubular member 10 and has a configuration corresponding to one half of the cross section of the plunger 16 of the syringe 12. As is the case with the embodiment shown in FIGS. 5-7, the closed terminus 28 of the slot 26 is adjacent to the cylindrical portion 20 and the open terminus 30 is at the small end of the tubular member 10. Furthermore, the web 37 is formed across a portion of the small end of the tubular member 10 adjacent to the slot 26 and defines therein the aperture 36 in alignment with and in communication with the slot 26, the aperture 36 having a configuration corresponding to the other half of the cross section of the plunger 16. A slit 46 extends from the aperture 36 in the web 37 to the edge 41 to define a pair of flaps abutting one another along the slit 46. The slot 26 in the frustoconical portion 22 and the aperture 36 in the web 37 cooperate to define an opening congruent to the cross sectional shape of the plunger 16.

As is shown in FIG. 9, as the plunger 16 of a syringe 12 is moved into the slit 46, the flaps bordering the slit 46 are forced apart, thereby allowing the plunger 16 to be moved further into the congruent opening in the web 37 and the frustoconical portion 22. After the plunger 16 has passed through the slit 46, the flaps move back into abutment with one another due to their own inherent resiliency. As can be seen from FIG. 10, the plunger 16 of the syringe 12 extends at an angle from the congruent opening in this embodiment of the digital device.

For all of the described embodiments, in use, the thumb of the user may be inserted into the digital device so that the tip of the thumb protrudes through the small end of the tubular member 10 and the knuckle of the thumb abuts the large end. With the digital device in position on the thumb of one hand, a user can grasp the syringe 12 with the other hand and can easily attach it to and detach it from the digital device as shown in FIG. 1. When the syringe 12 is attached to the digital device, the plunger 16 extends through the slot 26 with the head 18 of the plunger 16 positioned inside the tubular member 10 and in engagement with the thumb. When the needle of the syringe 12 has been inserted into the patient, the digital device is initially moved a small distance in a direction away from the syringe 12 and, due to the fact that the head 18 of the plunger 16 is greater in dimension than the slot 26, the plunger 16 moves with the thumb device in the retracting direction thus creating negative pressure within the barrel of the syringe 12. In addition, when the syringe 12 is being filled with a medicinal fluid, as from a vial, the digital device and the plunger 16 are moved in the retracting direction. In the injecting direction, a force is applied to the head 18 of the plunger 16 by the thumb, while the digital device aids in retaining the thumb in position on top of the head 18 and prevents the thumb from sliding off the sides of the head 18 as the force is applied.

Figure 11:
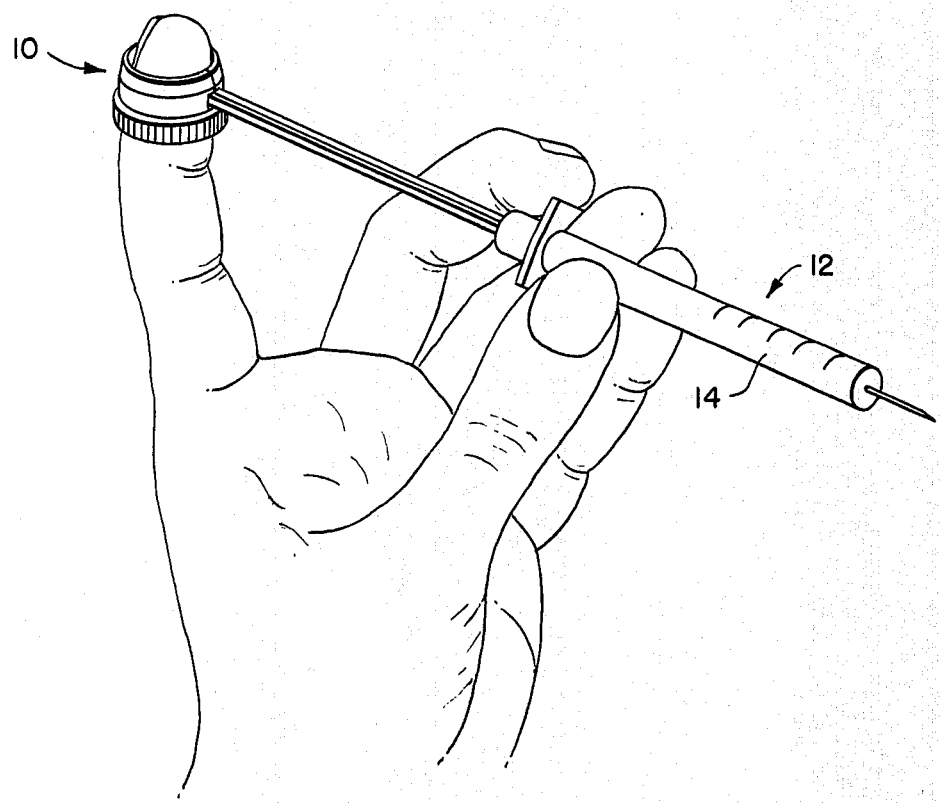
FIG. 11 illustrates an alternative method from that shown in FIG. 1 in which the index finger is inserted into the digital device of the invention and controls the movement of the syringe plunger.

The digital device, instead of being used on the thumb, may be used on the index finger, as shown in FIG. 11. When used this way, the thumb and forefingers of the person making the injection may grip the barrel 14 of the syringe 12 and the index finger may be inserted into the device 10, which thus secures the index finger to the head 18 of the plunger. In this manner, the index finger controls the withdrawal of the syringe plunger and the injection of the biological material.

Figure 12:
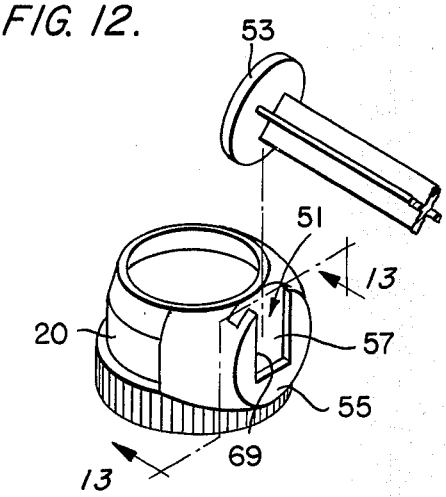
FIG. 12 shows a perspective view of another embodiment of the present invention designed for use with the large heads of the plungers of 3 cc. to 5 cc. syringes.
Figure 13:
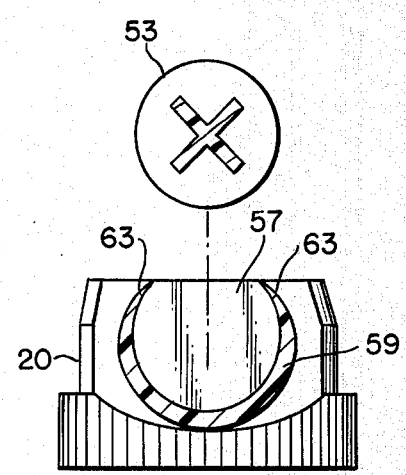
FIG. 13 is a sectional view taken along the line 13—13 of FIG. 12.

The embodiment of the invention shown in FIGS. 12 and 13 is designed for use with syringes which have large heads, such as a typical 3 cc. or 5 cc. syringe. In this embodiment, an opening to receive the head of the plunger is not defined through the wall of the cylindrical section 20 to avoid the aperture weakening the structural strength of the cylindrical member. Instead, the device is molded to define an aperture 51 outside the inner diameter of the cylindrical section 20 shaped to receive the enlarged head 53 of the syringe plunger. The aperture 51 is defined by an outer wall 55 spaced outwardly from a flat outwardly facing surface 57 of the cylindrical member 20. The outer wall 55 is joined to the surface 57 by the crescent shaped sidewall 59 as best shown in FIG. 13. The ends 63 of the widewall 59 define an opening to receive the head 53, which is slightly larger in diameter than the length of the opening between the ends 63. The resiliency of the material of sidewall 59 permits the head 53 to be pushed through the opening between the ends 63 of the sidewall 59 and the sidewall 59 will then hold the head 53 securely in position. The outer wall 55 is provided with a slot 69 extending to the edge of the wall 55 at the opening between the ends 63 of the sidewall 59 so as to accommodate the plunger 16 when the head 53 has been inserted into the aperture 51.

In all of the embodiments of the invention, the inwardly tapering frustoconical portion 22 assures that the digital device will fit snugly at the small, open end of the tubular member 10 on the tapered portion of the thumb or finger near the tip, as it does at the large open end of the tubular member 10 near the knuckle.

Although the foregoing describes various preferred embodiments according to the present invention, it is understood that various changes and modifications may be made without departing from the spirit and scope of the present invention as recited in the appended claims and their legal equivalent.

What is claimed is:

1. A digital device for attachment to a syringe having a barrel, a plunger having a first end positioned in the barrel for reciprocation therein and a second end external to the barrel and having a head connected thereto, said digital device comprising:
a unitary tubular member adapted to receive a thumb or finger of a user and having first and second open ends and a slot defined in the wall by said tubular member for receiving the plunger, said slot extending from a closed terminus intermediate the first and second ends of said tubular member to an open terminus at the second end of said tubular member.

2. The digital device of claim 1, wherein the size of the slot is greater than the width of the plunger but less than the size of the head of the plunger,
whereby, when the plunger is in an operative position on the digital device and the digital device is moved away from the syringe, the slot will prevent the head from separating from the digital device.

3. The digital device of claim 1, wherein a gripping formation is defined on the tubular member.

4. The digital device of claim 3, wherein the gripping formation comprises a radially outwardly extending annular flange.

5. The digital device of claim 1, wherein the slot has a constant width from the closed terminus to the open terminus.

6. The digital device of claim 1, wherein the slot further includes an opening adjacent to the closed terminus and a slit narrower than said opening extending from the opening of the slot to the open terinus of the slot.

7. The digital device of claim 1, wherein the slot has a configuration corresponding to one half of the cross section of the plunger, and a web is formed across a portion of the second open end of the tubular member adjacent to the slot, the web defining an aperture in alignment with and in communication with the slot and having a configuration corresponding to the other half of the cross section of the plunger.

8. The digital device of claim 7, wherein the web further defines an edge extending along a chord of the second end of the tubular member and a slit extending from the aperture in the web of the edge.

9. A digital device for attachment to a syringe having a barrel, a plunger having a first end positioned in the barrel for reciprocation therein and a second end external to the barrel and having a head connected thereto, said digital device comprising:
a unitary tubular member adapted to receive a thumb or finger of a user and having first and second open ends and a slot for receiving the plunger, said slot extending from a closed terminus intermediate the first and second ends of said tubular member to an open terminus at the second end of said tubular member, said slot including a stem portion extending from said open terminus to a transverse opening intermediate the first and second ends of said tubular member.

10. The digital device of claim 9, wherein said transverse opening has a configuration corresponding to the cross-section of the plunger.

11. The digital device of claim 9, wherein a web is formed across the second end of the tubular member adjacent to the open terminus of the slot, and an aperture contiguous with the slot of the tubular member is defined in the web.

12. The digital device of claim 11, wherein the aperture has a width equal to the width of the stem portion of the slot.

13. A digital device for attachment to a syringe having a barrel, a plunger having a first end positioned in the barrel for reciprocation therein and a second end external to the barrel and having a head connected thereto, said digital device comprising:
a unitary tubular member adapted to receive a thumb or finger of a user and having first and second open ends and a slot for receiving the plunger, said slot extending from a closed terminus intermediate the first and second ends of said tubular member to an open terminus at the second end of said tubular member, said tubular member including an inwardly tapering frusto-conical portion at the second open end thereof so that, when the digital device is in position on a thumb or finger, the second open end of the tubular member fits snugly around the tapering portion of the thumb or finger between the knuckle and the tip while the first open end of the tubular member fits snugly around the thumb or finger at the knuckle.

14. A digital device for attachment to a syringe having a barrel, a plunger having a first end positioned in the barrel for reciprocation therein and a second end external to the barrel comprising a shaft having a head connected thereto, said digital device comprising:
a tubular member adapted to receive a thumb or finger of a user, having first and second open ends, and having an axial length greater than the width of said head, and including means defining a slot for receiving said shaft with the head of the plunger adjacent to the wall of said tubular member, said slot extending from a closed terminus intermediate the first and second ends of said tubular member to an open terminus at the second end of said tubular member and being shaped to retain said shaft within said slot.

15. The digital device of claim 14, wherein said slot is positioned radially outward from the wall of said tubular member and a distal side of the head of the plunger is adjacent to the wall of said tubular member when the plunger is received in said slot.

* * * * *